United States Patent
Minamino et al.

(10) Patent No.: US 10,781,466 B2
(45) Date of Patent: Sep. 22, 2020

(54) METHOD OF PRODUCING SUGAR LIQUID

(71) Applicant: Toray Industries, Inc., Tokyo (JP)

(72) Inventors: Atsushi Minamino, Kamakura (JP); Yuka Asahi, Kamakura (JP); Hiroyuki Kurihara, Kamakura (JP); Jumpei Kishimoto, Masaki (JP); Masashi Higasa, Kamakura (JP); Katsushige Yamada, Kamakura (JP)

(73) Assignee: Toray Industries, Inc., Tokyo (JP)

( * ) Notice: Subject to any disclaimer, the term of this patent is extended or adjusted under 35 U.S.C. 154(b) by 0 days.

(21) Appl. No.: 15/508,558

(22) PCT Filed: Sep. 4, 2015

(86) PCT No.: PCT/JP2015/075165
§ 371 (c)(1),
(2) Date: Mar. 3, 2017

(87) PCT Pub. No.: WO2016/035875
PCT Pub. Date: Mar. 10, 2016

(65) Prior Publication Data
US 2017/0275663 A1 Sep. 28, 2017

(30) Foreign Application Priority Data
Sep. 5, 2014 (JP) .................. 2014-181320

(51) Int. Cl.
| C12P 19/14 | (2006.01) |
| C12P 19/02 | (2006.01) |
| C12P 19/12 | (2006.01) |
| B01D 61/14 | (2006.01) |
| B01D 61/16 | (2006.01) |

(52) U.S. Cl.
CPC ............ *C12P 19/14* (2013.01); *B01D 61/142* (2013.01); *B01D 61/145* (2013.01); *B01D 61/147* (2013.01); *B01D 61/16* (2013.01); *C12P 19/02* (2013.01); *C12P 19/12* (2013.01); *C12Y 302/01004* (2013.01); *C12Y 302/01025* (2013.01); *B01D 2311/04* (2013.01); *B01D 2311/263* (2013.01); *B01D 2311/2688* (2013.01); *B01D 2317/025* (2013.01); *C12P 2201/00* (2013.01)

(58) Field of Classification Search
None
See application file for complete search history.

(56) References Cited

U.S. PATENT DOCUMENTS

| 2008/0311245 A1 | 12/2008 | Silver et al. |
| 2011/0281013 A1 | 11/2011 | Silver et al. |
| 2013/0203117 A1* | 8/2013 | Kurihara ........... C12P 19/14 435/72 |
| 2014/0287461 A1 | 9/2014 | Kurihara et al. |
| 2014/0322764 A1* | 10/2014 | Yanai .............. C12N 9/248 435/99 |
| 2015/0125908 A1 | 5/2015 | Kurihara et al. |

FOREIGN PATENT DOCUMENTS

| JP | 63-137691 A | 6/1988 |
| JP | 8-317795 A | 12/1996 |
| JP | 2002-59118 A | 2/2002 |
| JP | 2009-501545 A | 1/2009 |
| JP | 2010-36058 A | 2/2010 |
| JP | 2011-223975 A | 11/2011 |
| JP | 2011-254753 A | 12/2011 |
| JP | 2012-214452 A | 11/2012 |
| WO | 2010/067785 A1 | 6/2010 |
| WO | 2011/115040 A1 | 9/2011 |
| WO | WO-2013077432 A1 * | 5/2013 |
| WO | 2013/172446 A1 | 11/2013 |

OTHER PUBLICATIONS

Sigma-Aldrich, "Steriflip® Filters", available online from the company's webpage "https://www.sigmaaldrich.com/technical-documents/articles/biology/steriflip-filters.html", copyright 2018, accessed Sep. 17, 2018 (Year: 2018).*
Rivas et al. "Manufacture and properties of bifidogenic saccharides derived from wood mannan." Journal of Agricultural and Food Chemistry 60.17 (2012): 4296-4305. (Year: 2012).*
Supplementary European Search Report dated Jan. 19, 2018, of corresponding European Application No. 15838167.3.
Liu, S., et al., "Membrane filtration: Concentration and purification of hydrolyzates from biomass," *Journal of Biobased Materials and Bioenergy*, vol. 2, No. 2, Jun. 1, 2008, pp. 121-134.
Cameron, H., et al., "Improved saccharification of steam-exploded *Pinus radiata* on supplementing crude extract of *Penicillium* sp.," *3 Biotech*, vol. 5, No. 2, Apr. 1, 2015, pp. 221-225.
Office Action dated May 23, 2019, of counterpart Indonesian Application No. P00201702149, along with an English translation.
Notification of Reason for Rejection dated Aug. 30, 2019, of counterpart Japanese Application No. 2015-545967, along with an English translation.
Office Action dated Feb. 17, 2020, of counterpart Indian Application No. 201747011297.

* cited by examiner

*Primary Examiner* — Emily A Cordas
(74) *Attorney, Agent, or Firm* — DLA Piper LLP (US)

(57) ABSTRACT

A method of producing a sugar liquid includes: (A) reacting mannanase with a liquid component obtained by hydrolysis treatment of woody biomass to obtain a saccharified liquid; and (B) filtering the saccharified liquid in Step (A) through a microfiltration membrane and/or ultrafiltration membrane to collect a sugar liquid from a permeate side.

9 Claims, 3 Drawing Sheets

METHOD OF PRODUCING SUGAR LIQUID

TECHNICAL FIELD

This disclosure relates to a method of efficiently producing a sugar liquid from woody biomass.

BACKGROUND

The process of fermentation production of chemical products using sugars as raw materials has been used to produce various industrial materials. At present, as the sugars to be used as fermentation feedstocks, those derived from food materials such as sugar cane, starch, and sugar beet are industrially used. However, in view of the fact that increases in the prices of food materials is expected due to future increases in the world population, or in an ethical view of the fact that those sugars compete with sugars for food, a process of efficiently producing a sugar liquid from a renewable nonfood resource, that is, cellulose-containing biomass, or a process of using an obtained sugar liquid as a fermentation feedstock to efficiently convert it to an industrial material, needs to be constructed in the future.

Cellulose-containing biomass can be roughly divided into herbaceous biomass and woody biomass. Woody biomass has so far been industrially utilized in the paper industry. However, because of factors such as the recent decrease in its demand due to the trend toward a paperless society, studies are being carried out for its utilization as a raw material for sugars (JP 2010-36058 A and JP 63-137691 A).

Cellulose-containing biomass mainly contains lignin, which is an aromatic polymer, and cellulose and hemicellulose, which are polymers of monosaccharides. Examples of known methods of obtaining a sugar liquid include methods in which cellulose and hemicellulose protected by lignin are mechanically or thermochemically hydrolyzed, and methods in which the mechanical or thermochemical hydrolysis is further followed by hydrolysis by saccharifying enzyme.

In production of sugar liquids from cellulose-containing biomass, there have been problems that cellulose-containing biomass contains a large amount of solid components and low-molecular-weight fermentation-inhibiting substances, and that a large amount of enzyme needs to be used, leading to a high production cost. Under such circumstances, methods based on processing of a sugar liquid by membrane separation are being studied. Examples of such methods include a method in which a sugar liquid is purified using a nanofiltration membrane or a reverse osmosis membrane (JP 2011-223975 A), a method in which solid-liquid separation is carried out using a microfiltration membrane (WO 2010/067785), and a method in which enzyme is recovered using an ultrafiltration membrane (JP 8-317795 A).

It could therefore be helpful to provide a method that increases the filtration performance during filtration of a woody-biomass-derived saccharified liquid through a microfiltration membrane and/or ultrafiltration membrane, to thereby provide a method of efficient production of a sugar liquid.

SUMMARY

We discovered that, when woody biomass is used as the cellulose-containing biomass, particular components contained in the woody-biomass-derived saccharified liquid cause marked deterioration of the filtration performance during filtration of the saccharified liquid through a microfiltration membrane and/or ultrafiltration membrane, and that, even when physical washing is carried out by changing the operating conditions, these components still cause deterioration of the long-term operability because of their high adhesiveness especially to polymer membranes.

We also discovered that the above-described components contained in a woody-biomass-derived saccharified liquid and causing marked deterioration of the filtration performance of a microfiltration membrane and/or ultrafiltration membrane, can be degraded by mannanase and that, as a result, the filtration performance of the microfiltration membrane and/or ultrafiltration membrane for the saccharified liquid can be increased.

We thus provide [1] to [10] below.

[1] A method of producing a sugar liquid, the method comprising the steps of:

(A) reacting mannanase with a liquid component obtained by hydrolysis treatment of woody biomass to obtain a saccharified liquid; and (B) filtering the saccharified liquid in Step (A) through a microfiltration membrane and/or ultrafiltration membrane to collect a sugar liquid from the permeate side.

[2] The method of producing a sugar liquid according to [1], wherein the woody biomass is coniferous biomass.

[3] The method of producing a sugar liquid according to [1] or [2], wherein the hydrolysis treatment in the Step (A) is one or more selected from the group consisting of hydrothermal treatment, steam explosion treatment, and dilute acid treatment.

[4] The method of producing a sugar liquid according to any one of [1] to [3], wherein, in the Step (A), cellulase is reacted with the liquid component.

[5] The method of producing a sugar liquid according to any one of [1] to [4], wherein, in the Step (A), the amount of mannanase added is not less than 0.01 Unit/g with respect to the total amount of mannose (g) contained in the liquid component.

[6] The method of producing a sugar liquid according to any one of [1] to [5], wherein a functional surface(s) of a material(s) of the microfiltration membrane and/or ultrafiltration membrane in the Step (B) is/are an organic membrane(s).

[7] The method of producing a sugar liquid according to any one of [1] to [6], wherein the microfiltration membrane in the Step (B) is a microfiltration membrane having an average pore size of 0.01 to 0.5 μm.

[8] The method of producing a sugar liquid according to any one of [1] to [7], wherein the ultrafiltration membrane in the Step (B) is an ultrafiltration membrane having a molecular weight cutoff of 5000 to 150,000.

[9] The method of producing a sugar liquid according to any one of [1] to [8], comprising the step of:

(C) filtering the sugar liquid obtained in the Step (B) through an ultrafiltration membrane having a molecular weight cutoff of 300 to 1000, to collect a sugar liquid containing mannobiose and/or mannotriose from the feed side, and to collect a sugar liquid containing a monosaccharide from the permeate side.

[10] A method of producing a sugar liquid, the method comprising, in the method of producing a sugar liquid according to any one of [1] to [9], the steps of:

carrying out ultrafiltration membrane treatment as Step (B); and carrying out Step (A) using an enzyme component(s) collected from the feed side of the ultrafiltration membrane.

A woody-biomass-derived saccharified liquid can be filtered through a microfiltration membrane and/or ultrafiltration membrane. Further, mannobiose and mannotriose can be produced as valuable substances during production of monosaccharides such as glucose and xylose as a fermentation feedstock. As a result, we contribute to reduction of the cost of producing chemical products using fermentation.

DESCRIPTION OF SYMBOLS

Figure 1:
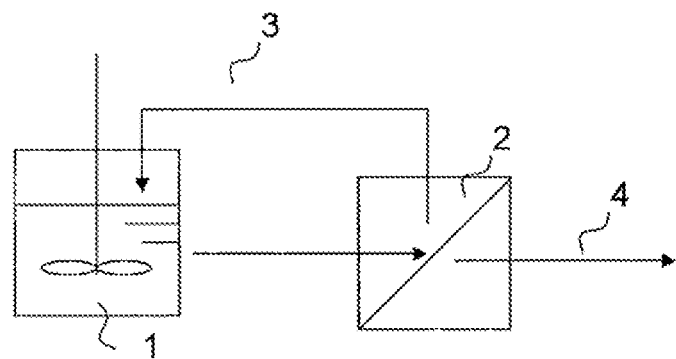
FIG. 1 shows a process flow schematically illustrating a method in which membrane filtration of a woody-biomass-derived saccharified liquid is carried out using the combination of a microfiltration membrane and an ultrafiltration membrane while mannanase and cellulase are recovered.

1 Enzymatic saccharification tank
2 Ultrafiltration membrane with a molecular weight cutoff of 5000 to 150,000
3 Recovered enzyme
4 Saccharified liquid
5 Microfiltration membrane
6 Solid component
7 Ultrafiltration membrane with a molecular weight cutoff of 300 to 1,000
8 Aqueous solution of mannobiose/mannotriose
9 Monosaccharide sugar liquid
10 Nanofiltration membrane/reverse osmosis membrane
11 Concentrated liquid for fermentation
12 Fermentation inhibitor

DETAILED DESCRIPTION

Woody biomass is biomass derived from perennial plants in which a large amount of xylem is formed by thickening growth due to division activity of the vascular cambium developed in the stem and the root, wherein a large proportion of the cell wall undergoes lignification to become solid. Specific examples of sources of woody biomass include wood for papermaking; remaining materials from paper mills and saw mills; unused thinnings; construction-derived wood; waste wood; waste paper, refuse paper, and recycled paper; wood chips; and bark.

In terms of the composition of woody biomass, it is constituted of cellulose, hemicellulose, lignin, ash content, and the like. According to "Advanced Technologies for Chemicals from Wood Resources" (CMC Publishing Co., Ltd.), examples of the hemicellulose include glucuronoxylan, arabinoglucuronoxylan, glucomannan, galactoglucomannan, arabinogalactan, galactan, and lignin-carbohydrate complexes. Investigation of the monosaccharide composition of cellulose and hemicellulose is possible by hydrolysis using concentrated sulfuric acid. Almost complete hydrolysis of sugars in cellulose and hemicellulose into monosaccharides produces, as a result of degradation, monosaccharides such as glucose, xylose, arabinose, mannose, and galactose. By this, the monosaccharide composition can be known. By subjecting cellulose and hemicellulose, which are polysaccharide components contained in biomass, to hydrolysis treatment and/or enzyme treatment, a sugar liquid containing monosaccharides that can be utilized as a fermentation feedstock can be produced.

Examples of the woody biomass mainly include coniferous biomass and broad-leaved tree biomass, and biomass of monocotyledons that show lignification.

In general, conifers are mainly distributed in cold areas, and most of them are evergreen trees. They have needle-shaped narrow leaves and tall and soft wood, and belong to Coniferae in Gymnospermae. More specifically, "conifers" means those having a mannose content of 2% by weight to 15% by weight in terms of the dry weight of the biomass. More specifically, examples of the conifers include *Cryptomeria japonica*, *Pinus*, *Abies*, *Larix kaempferi*, *Pinus densiflora*, *Pinus thunbergii*, *Taxus cuspidata*, *Ginkgo biloba*, *Podocarpus macrophyllus*, *Picea jezoensis*, *Torreya nucifera*, *Larix kaempferi*, *Sciadopitys verticillata*, *Chamaecyparis pisifera*, *Tsuga sieboldii*, *Pseudotsuga japonica*, *Abies sachalinensis*, *Thuja standisii*, *Chamaecyparis obtusa*, *Thujopsis dolabrata*, *Pinus parviflora*, spruce, *Thuja standishii*, *Callitris*, *Juniperus*, *Pherosphaera*, *Phyllocladus*, *Abies homolepis*, *Abies mariesii*, *Abies Veitchii*, *Picea jezoensis*, *Picea glehnii*, *Thuja standisii*, *Thujopsis dolabrata*, and *Pinus parviflora*. However, the species of the conifers are not limited to these.

On the other hand, broad-leaved trees are woody plants having broad and flat leaves, belonging to Angiospermae. In particular, the broad-leaved trees are those having a mannose content of less than 2% by weight. More specifically, examples of the broad-leaved trees include oak, *Populus suaveolens*, *Populus tremula*, *Juglans mandshurica*, *Pterocarya rhoifolia*, *Alnus hirsuta*, *Betula gross*, *Betula platyphylla*, *Betula maximowicziana*, *Carpinus laxiflora*, *Ostrya japonica*, *Castanea crenata*, *Castanopsis*, *Fagus crenata*, *Fagus japonica*, *Quercus acuta*, *Quercus myrsinifolia*, *Quercus gilva*, *Quercus acutissima*, *Quercus crispula*, *Quercus serrata*, *Ulmus davidian*, *Zelkova serrata*, *Morus australis*, *Cercidiphyllum japonicum*, *Magnolia obovata*, *Cinnamomum camphora*, *Machilus thunbergii*, *Distylium racemosum*, *Cerasus jamasakura*, *Maackia amurensis*, *Phellodendron amurense*, *Acer pictum*, *Aesculus turbinata*, *Tilia japonica*, *Tilia maximowicziana*, *Stewartia monadelpha*, *Kalopanax septemlobus*, *Cornus controversa*, *Fraxinus platypoda*, *Fraxinus mandshurica*, *Fraxinus lanuginosa*, *Paulownia tomentosa*, *Castanopsis cuspidata*, *Toisusu Urbaniana*, *Prunus*, *Eucalyptus*, Arecaceae, *Magnolia quinquepeta*, *Salix*, *Rhododendron*, *Juglans*, *Morella rubra*, Casuarinaceae, *Barringtonia racemosa*, and *Diospyros kaki*. However, the species of the broad-leaved trees are not limited to these.

Examples of the biomass of monocotyledons that show lignification include, but are not limited to, bamboo.

Examples of the woody biomass also include non-edible cellulose-based unused resources such as stem, bark, empty fruit bunch (which does not contain fruit or flesh) called EFB (Empty Fruit Bunches), wood chips, and bamboo waste.

The hydrolysis treatment means degradation of mainly hemicellulose components and lignin in woody biomass. By the hydrolysis treatment, these components are degraded into various fractions such as sugars including monosaccharides, oligosaccharides, and polysaccharides; polyphenols; aromatic/furan components; and organic acids. Examples of the hydrolysis treatment include hydrothermal treatment, steam explosion treatment, and dilute acid treatment.

The hydrothermal treatment is a method in which woody biomass is treated with pressurized hot water at 100 to 400° C. for 1 second to 60 minutes such that the woody biomass is contained at 0.1 to 50% by weight, without addition of acid. The temperature of the water brought into contact with the woody biomass to be treated is not limited. The pressure is not limited since it depends on the treatment temperature. The pressure is preferably 0.01 to 10 MPa.

In the hydrothermal treatment, the components eluted into the hot water may vary depending on the temperature during the treatment with water. According to JP 2002-59118, as the temperature of the pressurized hot water increases, elution of the first group, which includes tannin and lignin, first occurs from woody biomass, and then elution of the second group, which includes hemicellulose, occurs at not less than 140 to 150° C., followed by elution of the third group, which includes cellulose, at a temperature higher than about 230° C. Further, at the same time as the elution, hydrolysis of hemicellulose and cellulose may occur. It is said that, in this hydrolysis reaction, organic acids such as acetic acid and formic acid eluted from the biomass aid the hydrolysis treatment. For the purpose of, for example, increasing the efficiency of reaction of cellulose and hemicellulose with the later-described enzymes, the difference in the eluted components depending on the treatment temperature may be utilized to carry out a multistage reaction treatment with two or more stages at different treatment temperatures. Water containing a component eluted, at any temperature, into the pressurized hot water is referred to as "liquid component", and the portion prepared by removal of the liquid component from the cellulose-containing biomass after the hydrothermal treatment is referred to as "solid component". The method of separation of the liquid component from the solid component is not limited, and the temperature during the separation is also not limited. In the multistage reaction treatment with two or more stages, there may be two or more kinds of liquid components corresponding to different stages, and/or there may be a mixture of two or more of the liquid components. Although the solid component and the liquid component may be separated from each other, the degradation with enzyme (mannanase, cellulase, and/or the like) may be carried out either separately for each of the solid component and the liquid component of the biomass, or for a mixture of the solid component and the liquid component.

The steam explosion treatment means a method in which woody biomass is exposed to high-pressure water vapor, and then kept under high-pressure conditions at about 1 MPa to 5 MPa for 1 second to 10 minutes, followed by releasing the pressure to the atmospheric pressure at once. In general, similarly to the hydrolysis treatment, the high-pressure water vapor first causes elution of lignin. This is followed by hydrolysis of the hemicellulose component, which has low crystallinity, and then degradation of the cellulose component, which has high crystallinity. Further, the release of the pressure to the atmospheric pressure causes rapid disruption of the biomass tissue, which increases sites on which enzyme can react. The resulting pulverized biomass contains degradation products and excessively degraded products of lignin and sugars, as well as a large amount of solid components and compounds that inhibit fermentation. The inhibitory components can be removed from the solid component by carrying out solid-liquid separation by soaking the biomass in water, liquid reagent, or the like. By the solid-liquid separation, the biomass can be separated into the liquid component and the solid component. The degradation using enzyme (mannanase, cellulase, and/or the like) may be carried out for each of the solid component and the liquid component of the biomass after their separation from each other, or may be carried out for a mixture of the solid component and the liquid component.

The dilute acid treatment is a method in which woody biomass is treated with an acidic aqueous solution such as an aqueous solution of sulfuric acid or a sulfite, or with an aqueous organic acid solution, under high temperature and pressure. In general, in this method, lignin is first dissolved, followed by hydrolysis of the hemicellulose component, which has low crystallinity, and then degradation of the cellulose component, which has high crystallinity. Compared to the hydrothermal treatment, hydrolysis of cellulose and hemicellulose is particularly promoted so that the monosaccharide concentration tends to be high even at the same treatment temperature. Moreover, by setting two or more stages of steps, conditions suitable for hydrolysis of each of hemicellulose and cellulose can be set so that the degradation efficiency and the sugar yield can be increased. The type of the acid in the acid treatment is not limited as long as the acid causes hydrolysis. From an economic point of view, the acid is preferably sulfuric acid, acetic acid, citric acid, or lactic acid. The concentration of the acid is preferably 0.1 to 15% by weight, more preferably 0.5 to 5% by weight. The reaction temperature may be 100 to 300° C. The reaction time may be 1 second to 60 minutes. The number of times of the treatment is not limited, and the treatment may be carried out one or more times. Also by this treatment, the biomass can be separated into the liquid component and the solid component. The degradation with enzyme (mannanase, cellulase, and/or the like) may be carried out separately for each of the solid component and the liquid component of the biomass, or may be carried out for a mixture of the solid component and the liquid component. Since the solid component and the liquid component obtained by the acid treatment contain acid, they need to be subjected to neutralization before carrying out the hydrolysis by the saccharifying enzyme.

The hydrothermal treatment, steam explosion treatment, and dilute acid treatment may be carried out either individually or in combination. Preferably, any one of the treatments is carried out alone. The hydrothermal treatment is more preferred.

The liquid component obtained by the hydrolysis of woody biomass contains hemicellulose, lignin, tannin, and a part of the cellulose component obtained by elution as described above. On the other hand, the solid component mainly contains cellulose due to removal of most of lignin and the hemicellulose component. The liquid component and the solid component can be separated from each other by conventional solid-liquid separation.

Specific examples of the solid-liquid separation include filtration separation, centrifugation, and sedimentation. Centrifugation or filtration separation is preferred.

In centrifugation, acceleration is not limited. From the viewpoint of ease of the operation and the cost, acceleration is preferably 500 to 4000 G, more preferably 1000 to 3000 G. Specific examples of the apparatus include screw decanters.

Examples of the filtration method in the filtration separation include, but are not limited to, those using a screw press, screen filter, belt filter, belt press, or filter press. The separation may also be carried out using, instead of a solid-liquid separation device, a portion provided in the hydrolysis apparatus to be used for performing the hydrothermal treatment, steam explosion treatment, or dilute acid treatment, which portion has a function to carry out filtration separation through a screen or a mesh, sedimentation, or centrifugation.

The liquid component is treated with mannanase to obtain a saccharified liquid in Step (A). By the mannanase treatment of the liquid component, fouling substances derived from the woody biomass, which inhibits the later-described membrane treatment through a microfiltration membrane and/or ultrafiltration membrane, can be degraded, and, as a result, the filtration performance in the later-described membrane treatment through the microfiltration membrane and/or ultrafiltration membrane can be markedly increased compared to when the mannanase treatment is not carried out.

Mannanase is an enzyme containing an endo-type enzyme component that hydrolyzes the β-1,4 mannoside bond. Mannanase is produced by microorganisms. Either mannanase produced by a single kind of microorganism or mannanase produced by a plurality of kinds of microorganisms may be used. Specific examples of microorganisms which produce mannanase include microorganisms belonging to *Aspergillus*, *Trichoderma*, *Acremonium*, *Penicillium*, and *Bacillus*. Mannanases produced by microorganisms belonging to *Aspergillus* are especially preferably used since these mannanases have high activity. Examples of mannanases derived from microorganisms belonging to *Aspergillus* include "Mannanase BGM Amano", manufactured by Amano Enzyme Inc.; "Sumizyme ACH", manufactured by Shin Nippon Biomedical Laboratories, Ltd.; "Cellulosin GM5", manufactured by HBI Enzymes Inc.; and "Mannaway", manufactured by Novozymes Japan.

The amount of the mannanase added to the liquid component is not limited as long as the fouling substances can be degraded therewith. The amount is preferably not less than 0.01 Unit/g from the viewpoint of the fact that an effect to improve the filtration performance for the total amount of mannose (g) contained in the liquid component has been confirmed with such an amount. From an economic point of view, the amount is more preferably not more than 10,000 Units/g. The amount of the mannanase added is preferably 0.01 Unit/g to 10,000 Units/g, more preferably 0.1 Unit/g to 10,000 Units/g.

The total amount of mannose contained in the liquid component can be calculated by subjecting the liquid component to vacuum evaporation, and then subjecting the resulting product to forced complete hydrolysis to monosaccharides using concentrated sulfuric acid and dilute sulfuric acid according to description in NREL/TP-510-42618 "Determination of Structural Carbohydrates and Lignin in Biomass", followed by analyzing the amount of mannose using HPLC or the like. Mannanase has the highest reactivity with mannan, and its further addition hardly increases the effect. Thus, the above value is most preferred from the viewpoint of the cost of the mannanase used. The reaction with mannanase produces mannotriose, mannobiose, and mannose. Preferably, the mannanase does not contain mannosidase, or its content is not more than 1% relative to β-mannanase in terms of the activity. That is, even if mannan is totally degraded into the monosaccharide mannose, it is not utilized as a fermentation feedstock in the metabolism of the microorganism so that the cost increases due to separation and purification from the fermentation product, and liquid-waste treatment. The above condition thus allows production of valuable substances as mannotriose and mannobiose, which can be easily separated using a membrane(s).

The liquid component preferably contains cellulase as an enzyme that further promotes the effect of mannanase. The cellulase means an enzyme component that degrades cellulose, or aids degradation of cellulose. Specific examples of the enzyme component include cellobiohydrolase, endoglucanase, exoglucanase, β-glucosidase, xylanase, xylosidase, and biomass-swelling enzymes. The cellulase may be either cellulase produced by a single kind of microorganism, or cellulase produced by a plurality of kinds of microorganisms. As the cellulase produced by the microorganism(s), cellulase derived from a filamentous fungus/fungi belonging to *Trichoderma* or *Acremonium* is preferably used. Examples of such cellulase include "CELLIC CTEC" and "CELLIC HTEC" series, manufactured by Novozymes; "ACCELLERASE" series, manufactured by Danisco Japan; "Cellulase from *Trichoderma reesei* ATCC 26921", "Cellulase from *Trichoderma viride*", and "Cellulase from *Trichoderma longibrachiatum*", manufactured by Sigma Aldrich; and "Meicelase", "*Acremonium* Cellulase", "ENM-3064", "ENM-0814", and "ENM-0115", manufactured by Meiji Seika Pharma Co., Ltd.

The types and the component ratios of the enzyme components in the cellulase are not limited. For example, a culture liquid derived from *Trichoderma reesei* contains cellobiohydrolase, β-glucosidase, and the like. Since β-glucosidase is retained in the cell or on the cell surface, the β-glucosidase activity in the culture liquid is low. In such a case, a different kind or the same kind of β-glucosidase may be further added to the culture supernatant.

Cellulase promotes the effect of mannose, and has an effect to allow production of monosaccharides such as glucose and xylose by the enzymatic reaction of the cellulase with hemicellulose contained in the liquid component. Thus, by separating monosaccharides from mannobiose and mannotriose by the later-mentioned membrane separation, and using the mannobiose and mannotriose as valuable substances for food, feed and the like, monosaccharides as a fermentation feedstock can be inexpensively produced.

In Step (A), the order of addition of the cellulase and the mannanase is not limited. A method in which cellulase is added to the liquid component, and the reaction is then allowed to proceed, followed by addition of mannanase, or a method in which cellulase and mannanase are added at once, is usually carried out.

Since the saccharified liquid obtained in Step (A) contains impurities derived from the woody biomass, the saccharified liquid is filtered through a microfiltration membrane and/or ultrafiltration membrane to collect a sugar liquid from the permeate side in Step (B).

The method of the filtration through a microfiltration membrane and/or ultrafiltration membrane is not limited. The method is preferably cross-flow filtration. Treatment of the liquid component with mannanase does not allow total degradation of the fouling component in the membrane treatment, and the fouling component partially remains. However, long-term operability of the membrane can be secured in the cross-flow filtration since a horizontal flow can be formed to reduce deposition on the membrane surface. When the solid component is present at a concentration of as high as not less than about 5% by weight, channel clogging may occur to prevent contact of the liquid itself on the membrane surface. In such cases, a solid-liquid separation step may be provided before the filtration through a microfiltration membrane and/or ultrafiltration membrane to avoid the risk of channel clogging. Specific examples of the method of the solid-liquid separation include, but are not limited to, filtration separation, centrifugation, and sedimentation. Centrifugation or filtration separation is preferred since filtration separation using a metal net, woven fabric, or non-woven fabric is hardly effective for removal of the solid component. The method of the solid-liquid separation is preferably centrifugation from the viewpoint of the space required for the device, and the cost of the device.

A microfiltration membrane is a membrane having a porous functional surface. The porous microfiltration membrane means a membrane having, in the functional surface, a sponge-shaped three-dimensional network structure in which voids are formed such that they communicate with each other. For example, membranes whose functional surface is a woven fabric or non-woven fabric are not included. It should be noted that the microfiltration membrane may contain a woven fabric or non-woven fabric in its base material which is not a functional surface.

The microfiltration membrane is preferably a microfiltration membrane having an average pore size of 0.01 to 0.5 µm. When the average pore size of the microfiltration membrane is 0.01 to 0.5 µm, membrane fouling can be effectively reduced when ultrafiltration membrane treatment, nanofiltration membrane treatment, and/or reverse osmosis membrane treatment is/are carried out as post-treatment of the microfiltration membrane treatment. As the average pore size of the microfiltration membrane, the nominal pore size presented by each separation membrane manufacturer may be employed, or the average pore size may be actually measured. As a method of measuring the average pore size of the microfiltration membrane, the direct observation method or the bubble point method may be applied. The average pore size is measured using the bubble point method. In the bubble point method, an air pressure is applied from the secondary side of the membrane, and the minimum pressure at which generation of an air bubble can be observed on the membrane surface is measured. According to a relational expression between the surface tension of the liquid used and the pressure, the average pore size is calculated. This method enables measurement according to ASTM F316-03. The measurement of the average pore size of the microfiltration membrane according to ASTM F316-03 can be carried out by, for example, using a penetrating-pore distribution/gas permeability analyzer manufactured by Bel Japan, Inc.

Examples of the material of the microfiltration membrane that may be employed include organic membranes (for example, cellulose-based membranes, aromatic polyamide, polyvinyl alcohol, polysulfone, polyvinylidene fluoride, polyethylene, polyacrylonitrile, polypropylene, polycarbonate, and polytetrafluoroethylene), ceramics, and metals. Organic membranes are preferred since they have marked membrane fouling effect by mannanase and cellulase. Polyvinylidene fluoride is especially preferred.

The ultrafiltration membrane means a membrane having a molecular weight cutoff of 300 to 200,000, and is referred to as ultrafiltration, UF membrane or the like for short. In the ultrafiltration membrane, the pore size on the membrane surface is too small to measure under the electron microscope or the like so that a value called "molecular weight cutoff" is used as an index of the pore size instead of the average pore size. In Membrane Society of Japan ed., Membrane Experiment Series, Vol. III, Artificial Membrane, editorial committee members: Shoji Kimura, Shin-ichi Nakao, Haruhiko Ohya, and Tsutomu Nakagawa (1993, Kyoritsu Shuppan Co., Ltd.), p. 92, there is the following description: "The curve obtained by plotting the molecular weight of the solute along the abscissa and the blocking rate along the ordinate is called 'molecular weight cutoff curve'. The molecular weight at which the blocking rate reaches 90% is called 'molecular weight cutoff of the membrane'." Thus, the molecular weight cutoff is well known to those skilled in the art as an index representing the membrane performance of an ultrafiltration membrane.

The material of the ultrafiltration membrane is not limited as long as the membrane has functions to allow removal of particulates and recovery of enzymes (mannose, cellulase, and the like). Examples of the material of the ultrafiltration membrane include organic membranes (for example, organic materials such as cellulose, cellulose ester, polysulfone, polyethersulfone, chlorinated polyethylene, polypropylene, polyolefin, polyvinyl alcohol, polymethyl methacrylate, polyvinylidene fluoride, and polytetrafluoroethylene), metal membranes (for example, stainless steel), and ceramic materials (for example, alumina and zirconia). Organic membranes are preferred since they have marked membrane fouling effect by mannanase and cellulase. Polyvinylidene fluoride, polysulfone, and polyethersulfone are especially preferred.

The form of the ultrafiltration membrane is not limited, and the membrane may be either a flat membrane or a hollow fiber membrane. When the saccharified liquid is filtered through an ultrafiltration membrane, the enzyme components (mannanase and cellulase) reacted with the liquid component can also be recovered so that the processing cost can be largely reduced. The enzyme components have molecular weights of 5000 to 150,000. By using an ultrafiltration membrane having a molecular weight cutoff with which the enzyme components can be blocked, more specifically, by using an ultrafiltration membrane having a molecular weight cutoff of 5000 to 150,000, the enzyme components can be recovered from the feed side. Examples of the ultrafiltration membrane having a molecular weight cutoff of 5000 to 150,000 include "TORAYFIL" HFU series, manufactured by Toray Industries, Inc.; "MICROZA" AIP series, ACP series, AHP series, SIP series, and SLP series, manufactured by Asahi Kasei Corporation; GM series, PW series, and HWS series, manufactured by DESAL; GR40PP, GR51PP, GR60PP, GR61PP, GR81 PP, and ETNA10PP, manufactured by Alfa-Laval; FS series and RC series, manufactured by DSS; ED, manufactured by AMT; PES10K, manufactured by Applied Membrane; HFM-180, HFM-183, HFM-251, HFP-276, HFM-300, HFM-116, HFM-131, HFM-328, PM5K, PM10K, PM30K, PM50K, PM100K, CM, XM5K, XM8K, MPT-U20, MPT-U20P, and MPT-U20S, manufactured by KOCH; and SPE5, SPE10, SPE30, SPE100, SPV5, SPV50, SPV100, and SOW30, manufactured by Synder.

Figure 2:
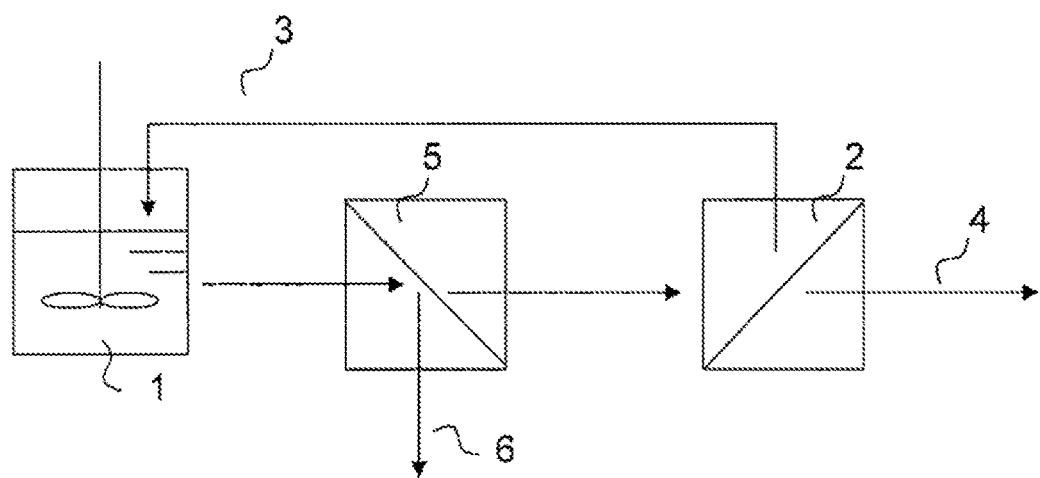
FIG. 2 shows a process flow schematically illustrating a method in which membrane filtration of a woody-biomass-derived saccharified liquid is carried out using an ultrafiltration membrane while mannanase and cellulase are recovered.

The recovered enzyme components may be reused by performing the reaction before the microfiltration membrane and/or ultrafiltration membrane treatment to reduce the amount of the enzyme used in Step (A). In particular, when an ultrafiltration membrane is used in Step (B), the liquid component of the woody biomass may be continuously fed to the enzyme component recovered from the feed side of the ultrafiltration membrane as shown in FIGS. 1 and 2. Since, by this, Step (A) and Step (B) can be continuously carried out, reduction of the equipment cost by the continuous process is possible.

Figure 3:
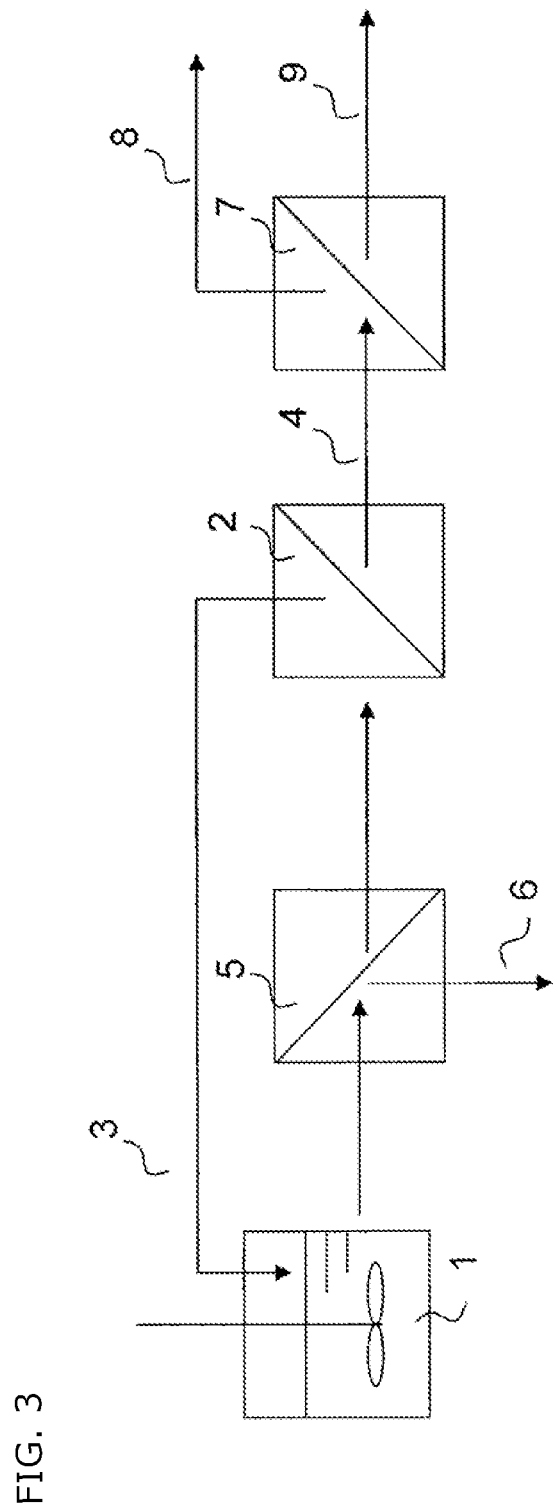
FIG. 3 shows a process flow schematically illustrating a method in which the permeate from the microfiltration membrane and/or ultrafiltration membrane obtained is subjected to treatment using an ultrafiltration membrane having a molecular weight cutoff of 300 to 1000, to separate monosaccharides from mannobiose and mannotriose.

The permeate from the microfiltration membrane and/or ultrafiltration membrane is preferably further subjected to treatment with an ultrafiltration membrane having a molecular weight cutoff of 300 to 1000 as Step (C) as shown in FIG. 3. By carrying out this treatment, mannobiose and mannotriose produced by the degradation by mannanase can be separated into the feed side of the membrane, and monosaccharides such as glucose and xylose can be separated into the permeate side of the membrane. As a result, the non-permeate components can be used for food and feed, and the permeate components can be used as a fermentation feedstock. Examples of the material of the ultrafiltration membrane having a molecular weight cutoff of 300 to 1000 that may be used include organic membranes (aromatic polyamide, piperazine polyamide, polyvinyl alcohol, polysulfone, polyether sulfone, sulfonated polysulfone, polyvinylidene fluoride, polyethylene, polyacrylonitrile, polypropylene, polycarbonate, and polytetrafluoroethylene), ceramics, and metals. From the viewpoint of controlling the pore size, aromatic polyamide, piperazine polyamide, polyvinyl alcohol, and sulfonated polysulfone are preferred. The form of the ultrafiltration membrane is not limited, and may be any of a spiral type, hollow fiber type, tubular type, and flat membrane type.

Specific examples of the ultrafiltration membrane having a molecular weight cutoff of 300 to 1000 include the G-5 type and GE type, manufactured by DESAL; SPE1, manufactured by Synder; PM1000, PM2000, MPS-36, and SR2, manufactured by KOCH; GR95Pp and ETNA01PP, manufactured by Alfa-Laval; NTR-7450 (molecular weight cutoff, 600 to 800; described in WaterResearch 37 (2003) 864-872) and NTR-7410 (molecular weight cutoff, 1,000; described in Collection of Papers for 5th Sanitary Engineering Symposium, 6-4), manufactured by Nitto Denko Corporation; and NFG (molecular weight cutoff, 600 to 800) and NFW (molecular weight cutoff, 300 to 500), manufactured by Synder. The form of the ultrafiltration membrane having a molecular weight cutoff of 300 to 1000 is not limited, and may be any of a spiral type, hollow fiber type, tubular type, and flat membrane type.

The means of purifying mannobiose and mannotriose is not limited to those described above. For example, fermentation may be carried out in a state where monosaccharides are mixed with mannobiose and mannotriose, and the liquid after consumption of glucose and xylose may be used for recovering mannobiose and mannotriose from the liquid using an ultrafiltration membrane having a molecular weight cutoff of 300 to 1000.

Figure 4:
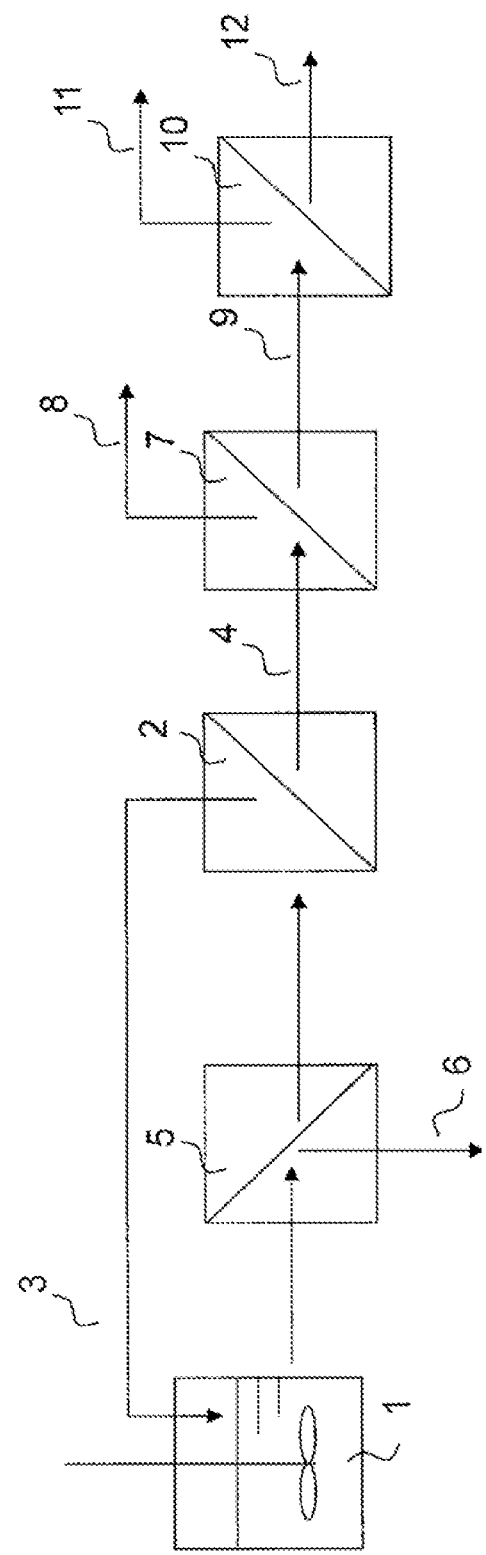
FIG. 4 shows a process flow schematically illustrating a method in which a monosaccharide concentrate is obtained from a permeate obtained by treatment using an ultrafiltration membrane having a molecular weight cutoff of 300 to 1000.

The permeate from the microfiltration membrane and/or ultrafiltration membrane is preferably filtered through a nanofiltration membrane and/or reverse osmosis membrane to concentrate monosaccharides contained in the permeate. More specifically, in such a method, as shown in FIG. 4, the permeate from the microfiltration membrane and/or ultrafiltration membrane is once treated with an ultrafiltration membrane having a molecular weight cutoff of 300 to 1000, and the resulting permeate is further subjected to treatment with a nanofiltration membrane and/or reverse osmosis membrane to obtain, as the non-permeate of the membrane, a sugar concentrate containing mainly monosaccharides. As described in WO 2010/067785, the concentration of monosaccharides with a nanofiltration membrane and/or reverse osmosis membrane has a function to remove fermentation-inhibiting substances such as formic acid, acetic acid, HMF, furfural, and vanillin contained in the liquid component into the membrane permeate side, while at the same time concentrating the monosaccharides.

The nanofiltration membrane is a membrane which is also called "nanofilter" (or "NF membrane"), and generally defined as a "membrane that allows permeation of monovalent ions, but blocks divalent ions". The membrane has fine voids having sizes of about several nanometers, and used mainly to block fine particles, molecules, ions, salts, and/or the like in water. Specific examples of the nanofiltration membrane include "GEsepa" DK series and HL series, manufactured by GE Osmonics; NF99 and NF99HF, manufactured by Alfa-Laval; NF, NF-45, NF-90, NF-200, NF-270, and NF-400, manufactured by Filmtec Corporation; and SU-200 series and SSU-600 series (such as SU610 and SU620), manufactured by Toray Industries, Inc. Specific examples of the nanofiltration membrane also include NTR769SR, NTR-729HF, NTR7250, and NTR-725HF, manufactured by Nitto Denko Corporation.

A reverse osmosis membrane is also called "RO membrane", and generally defined as a "membrane having a desalting function also for monovalent ions". The membrane has ultrafine voids having sizes ranging from about several angstroms to several nanometers, and mainly used for removal of ionic components such as seawater desalination and production of ultrapure water.

Specific examples of the reverse osmosis membrane include: an ultralow-pressure type series SUL-G, low-pressure type series SU-700, high-pressure type series SU-800, and cellulose acetate-type series SC-L100R, SC-L200R, SC-1000, SC-2000, SC-3000, SC-3200, and SC-8000, manufactured by Toray Industries, Inc.; NTR-759HR, NTR-70SWC, ES10-D, ES20-D, ES20-U, ES15-D, ES15-U, and LF10-D, manufactured by Nitto Denko Corporation; RO98pHt, R099, HR98PP, and CE4040C-30D, manufactured by Alfa-Laval; GE Sepa, manufactured by GE; BW30-4040, TW30-4040, XLE-4040, LP-4040, LE-4040, SW30-4040, and SW30HRLE-4040, manufactured by FilmTec Corporation; TFC-HR and TFC-ULP, manufactured by KOCH; ACM-1, ACM-2, and ACM-4, manufactured by TRISEP; and HA5330, HS5330, HKC3035, HS5205A, and CM10, manufactured by Toyobo Co. Ltd.

The forms of the nanofiltration membrane and the reverse osmosis membrane to be used are not limited, and may be any of a spiral type, hollow fiber type, tubular type, and flat membrane type.

The monosaccharides obtained are used in production of chemical products by fermentation. The chemical product produced by the fermentation step is not restricted as long as it is a substance produced into the culture liquid by the above microorganism or cells. Specific examples of the chemical product include alcohols, organic acids, amino acids, and nucleic acids, which are substances mass-produced in the fermentation industry. Examples of the alcohols include ethanol, butanol, 1,3-propanediol, 2,3-propanediol, 1,4-butanediol and glycerol; examples of the organic acids include acetic acid, lactic acid, pyruvic acid, succinic acid, malic acid, itaconic acid, and citric acid; examples of the nucleic acids include nucleosides such as inosine and guanosine, and nucleotides such as inosinic acid and guanylic acid; and diamine compounds such as cadaverine. Our methods may be applied also to production of substances such as enzymes, antibiotics, and recombinant proteins.

EXAMPLES

Reference Example 1 Method of Measuring Sugar Concentrations

Analysis of the sugar concentrations (glucose concentration, xylose concentration, and concentrations of mannobiose and mannotriose) in the sugar liquids obtained in Examples and Comparative Examples was carried out by HPLC under the following conditions, and quantification of sugars was carried out based on comparison with standard samples.

Column: ASAHIPAK NH2P-50 4E (manufactured by Shodex)
Mobile phase: ultrapure water:acetonitrile=25:75 (flow rate, 1.0 mL/min.)
Reaction liquid: phenylhydrazine
Detection method: fluorescence detection
Temperature: 30° C.

Reference Example 2 Method of Measuring Concentrations of Furan/Aromatic Compounds Analysis of the concentrations of furan compounds (HMF and furfural) and phenol compounds (vanillin and the like) contained in the sugar liquid was carried out by HPLC under the following conditions, and quantification of these compounds was carried out based on comparison with standard samples.

Column: SYNERGI HIDRORP 4.6 mm×250 mm (manufactured by Phenomenex, Inc.)
Mobile phase: Acetonitrile—0.1% $H_3PO_4$ (flow rate, 1.0 mL/min.)
Detection method: UV (283 nm)
Temperature: 40° C.

Reference Example 3 Method of Measuring Organic Acid Concentrations

Analysis of organic acids (acetic acid and formic acid) contained in the sugar liquid was carried out by HPLC under the following conditions, and quantification of these organic acids was carried out based on comparison with standard samples.

Column: Shim-Pack SPR-H and Shim-Pack SCR101H (manufactured by Shimadzu Corporation) that are linearly arranged
Mobile phase: 5 mM p-toluenesulfonic acid (flow rate, 0.8 mL/min.)
Reaction solution: 5 mM p-toluenesulfonic acid, 20 mM Bis-Tris, 0.1 mM EDTA.2Na (flow rate: 0.8 mL/min.)
Detection method: Electric conductivity
Temperature: 45° C.

Reference Example 4 Method of Measuring Turbidity

The turbidity of each sugar liquid was quantified using a high-performance laboratory turbidimeter (2100N) manufactured by HACH. Since this turbidimeter is applicable only to measurement of turbidities of not more than 1000 NTU, the sugar liquid was diluted with distilled water, if necessary, before the measurement. The resulting measured value was divided by the dilution rate to provide the turbidity.

Reference Example 5 Method of Measuring SS Concentration

The SS concentration of the sugar liquid was measured according to JIS K0102 14.1 (2008). Glass fiber filter paper (manufactured by ADVANTEC; GS-25) was heated at 105° C. for 2 hours, and then the weight of the glass fiber filter paper (weight a) was measured. The dried glass fiber filter paper was placed in a filtration filter holder (manufactured by ADVANTEC; KP-47S), and then suction filtration of V mL of a sample liquid (2 to 10 mL) was carried out. The glass fiber filter paper was heated again at 105° C. for 2 hours, and its weight (weight b) was then measured, followed by calculating the MLSS concentration according to Equation (1).

$$SS \text{ concentration [mg/L]} = (b-a) \text{ [mg]}/V \text{ [mL]} \times 1000 \quad (1)$$

Reference Example 6 Method of Measuring Total Concentration of Mannose Contained in Liquid Component With reference to the LAP method published by NREL ("Determination of Structural Carbohydrates and Lignin in Biomass, Laboratory Analytical Procedure (LAP)"), analysis of the composition was carried out by the following method.

An appropriate amount of a sample was taken, and kept at 120° C. using an infrared moisture meter (FD-720, manufactured by Kett Electric Laboratory). By a value obtained from the difference between the stable value after evaporation and the initial value, the moisture content was measured.

Subsequently, the analysis liquid was dried under vacuum on a stainless-steel tray, and the whole sample was then peeled off from the tray. The sample was then subjected to absolute-dry-weight correction to calculate the absolute-dry-weight-based content of each component. To 0.3 g of the absolute-dried analysis sample, 3 mL of 72% sulfuric acid was added, and the resulting mixture was stirred at 30° C. for 1 hour. The resulting reaction liquid was transferred with 84 mL of purified water to a pressure bottle, and subjected to degradation by heating using an autoclave at 120° C. for 1 hour. Thereafter, the degradation liquid and the residue were separated from each other by filtration. The filtrate and a washing liquid from the residue were combined, and the volume of the resulting mixture was adjusted to 100 mL to provide a sample liquid. Monosaccharides (xylose, mannose, and glucose) in the sample liquid were quantified by the method in Reference Example 1. From the monosaccharide concentrations in the obtained degradation liquid and the amount of the absolute-dried sample degraded, and from the amounts of constituent sugars in the analysis liquid, the content of mannose as one item thereof was calculated. By also using the moisture content value measured in advance, the total concentration of mannose present in the liquid component was determined by calculation according to Equation (1).

The amount of mannose as a constituent sugar was subjected to correction using an excessive-sugar-degradation correction factor upon degradation by heating (Sf, survival factor; 1.06 in cases of mannose).

$$\text{Total mannose concentration (g/L)} = (100 - \text{moisture content (\%)}) \times \text{mannose content (\%)}) \div 10 \quad (1)$$

Example 1 Liquid Component of Hydrolysate (Hydrothermally Treated Liquid) Produced by Hydrothermal Treatment of Woody Biomass The method of hydrolysis of the woody biomass by the hydrothermal treatment in Step (1) is described below by way of an example. As the woody biomass, three kinds of wood chips, that is, wood chips of conifers *Cryptomeria japonica* and *Pinus*, as well as wood chips of a broad-leaved tree *Eucalyptus*, were used. The woody biomass was soaked in water, and processed using an autoclave (manufactured by Nitto Koatsu Co., Ltd.) at 200° C. for 10 minutes with stirring. After the treatment, the biomass was allowed to cool to 50° C., and centrifugation (1500 G) was carried out to perform solid-liquid separation into the liquid component (hereinafter referred to as "hydrothermally treated liquid") and the solid component. The pH of each hydrothermally treated liquid was 3.8. The concentrations observed for each hydrothermally treated liquid were as follows. Components in each hydrothermally treated liquid are shown in Table 1, and the turbidity, the SS concentration, and the total mannose concentration are shown in Table 2.

TABLE 1

Composition of the hydrothermally treated liquid

| Analyzed item | Unit | Cryptomeria japonica | Pinus | Eucalyptus |
|---|---|---|---|---|
| Xylose | g/L | 5.0 | 4.4 | 17.0 |
| Mannose | g/L | 1.6 | 2.4 | 1.2 |
| Glucose | g/L | 0.5 | 1.2 | 2.5 |
| Mannobiose | g/L | 1.5 | 1.2 | 0.6 |
| Mannotriose | g/L | 0.9 | 0.6 | 0.6 |
| Acetic acid | g/L | 2.0 | 1.6 | 1.2 |
| Formic acid | g/L | 0.7 | 0.4 | 0.6 |
| HMF | g/L | 0.6 | 0.8 | 0.1 |
| Furfural | g/L | 1.2 | 1.1 | 3.2 |

TABLE 2

Turbidity and SS concentration of the hydrothermally treated liquid

| Analyzed item | Unit | Cryptomeria japonica | Pinus | Eucalyptus |
|---|---|---|---|---|
| Turbidity | NTU | 1616 | 1848 | 2420 |
| SS concentration | g/L | 4988 | 5056 | 7246 |
| Total mannose concentration | g/L | 28 | 30 | 10 |

Subsequently, the pH of each hydrothermally treated liquid was adjusted to 5.0 using an aqueous sodium hydroxide solution. The resulting liquid was divided into two portions, and 0.2 g of mannanase "Mannanase BGM (Amano)" (manufactured by Amano Enzyme Inc.) was added to one of these portions (liquid volume, 1 L), and 0.2 g of "Mannanase BGM (Amano)" (manufactured by Amano Enzyme Inc.) as well as 2 mL of cellulase "ACCELLERASE DUET" (manufactured by Danisco Japan) were added to the other portion (liquid volume, 1 L). The enzyme reaction was carried out at 50° C. for 24 hours. The resulting liquids are referred to as Saccharified Liquid A and Saccharified Liquid B, respectively. Originally, measurement by cross-flow filtration should be carried out, but, for simplicity of the study, the solid component was once mostly removed by centrifugation at 6000 G, and then dead-end filtration was carried out as an accelerated test using a microfiltration membrane "MEMBRAY TMR140" (registered trademark) (pore size, 0.08 μm), which is a flat membrane whose material is PVDF, manufactured by Toray Industries, Inc., to evaluate the filtration performance of the microfiltration membrane. The membrane was cut into a disk shape having a diameter of 4 mm to provide the filtration area before use. To obtain an index for evaluating the filtration performance, the membrane surface was kept immersed in the liquid while a pressure of 50 kPa was applied thereto. The amount of the liquid that could be filtered during the period from Minute 0 to Minute 1 after the beginning of the pressurization, and the amount of the liquid that could be filtered during the period from Minute 1 to Minute 2 (that is, during the following 1-minute period), were measured. The results on the turbidity before the filtration and the amount of the liquid filtered for each sample are shown in Table 3 (for Saccharified Liquid A) and Table 4 (for Saccharified Liquid B). The amount of the mannanase added for the preparation of Saccharified Liquid A or B was 71 Units/g in *Cryptomeria japonica*, 67 Units/g in *Pinus*, and 200 Units/g in *Eucalyptus*, with respect to the total amount of mannose (g) contained in the liquid component.

TABLE 3

Results of filtration through a microfiltration membrane (Saccharified Liquid A)

| Analyzed item | Unit | Cryptomeria japonica | Pinus | Eucalyptus |
|---|---|---|---|---|
| Amount of filtrate (0 to 1 min) | mg | 17.6 | 16.0 | 9.6 |
| Amount of filtrate (1 to 2 min) | mg | 14.4 | 14.4 | 6.4 |
| Turbidity before filtration | NTU | 150 | 172 | 252 |

TABLE 4

Results of filtration through a microfiltration membrane (Saccharified Liquid B)

| Analyzed item | Unit | Cryptomeria japonica | Pinus | Eucalyptus |
|---|---|---|---|---|
| Amount of filtrate (Minute 0 to Minute 1) | mg | 24.0 | 24.0 | 24.0 |
| Amount of filtrate (1 to 2 min) | mg | 17.6 | 19.2 | 19.2 |
| Turbidity before filtration | NTU | 146 | 162 | 132 |

To 1 L of each of the hydrothermally treated liquids of *Cryptomeria japonica* and *Pinus* (pH 5) obtained in Example 1, 2 mL of cellulase "ACCELLERASE DUET" (manufactured by Danisco Japan) was added, and the enzyme reaction was allowed to proceed at 50° C. for 24 hours, to obtain Saccharified Liquid C. After mostly removing the solid component from the hydrothermally treated liquids of *Cryptomeria japonica*, *Pinus*, and *Eucalyptus* (pH 5) obtained in Example 1, and Saccharified Liquids C (*Cryptomeria japonica* and *Pinus*) by centrifugation at 6000 G, dead-end filtration was carried out as an accelerated test using a microfiltration membrane "MEMBRAY TMR140" (registered trademark) (pore size, 0.08 μm), which is a flat membrane whose material is PVDF, manufactured by Toray Industries, Inc., to evaluate the filtration performance of the microfiltration membrane. The membrane was cut into a disk shape having a diameter of 4 mm to provide the filtration area before use. To obtain an index for evaluating the filtration performance, the membrane surface was kept immersed in the liquid while a pressure of 50 kPa was applied thereto. The amount of the liquid that could be filtered during the period from Minute 0 to Minute 1 after the beginning of the pressurization, and the amount of the liquid that could be filtered during the period from Minute 1 to Minute 2 (that is, during the following 1-minute period), were measured. The results are shown in Tables 5 and 6.

From the results, we found that the application of the microfiltration membrane is extremely difficult when no enzyme is added, or only cellulase is added.

TABLE 5

Results of filtration through a microfiltration membrane
(hydrothermally treated liquid, no addition of enzyme)

| Analyzed item | Unit | Cryptomeria japonica | Pinus | Eucalyptus |
|---|---|---|---|---|
| Amount of filtrate (0 to 1 min) | mg | 1.1 | 1.1 | 1.6 |
| Amount of filtrate (1 to 2 min) | mg | 1.0 | 1.0 | 1.2 |
| Turbidity before filtration | NTU | 235 | 240 | 300 |

TABLE 6

Results of filtration through a microfiltration membrane
(Saccharified Liquid C, addition of only cellulase)

| Analyzed item | Unit | Cryptomeria japonica | Pinus |
|---|---|---|---|
| Amount of filtrate (0 to 1 min) | mg | 1.1 | 1.1 |
| Amount of filtrate (1 to 2 min) | mg | 1.0 | 1.0 |
| Turbidity before filtration | NTU | 225 | 230 |

Comparative Example 2 Cases of Filtration Through Woven Fabric, Screen, or Non-Woven Fabric The hydrothermally treated liquids of *Cryptomeria japonica* and *Eucalyptus* (pH 5) obtained in Example 1 and Saccharified Liquid A were centrifuged at 6000 G to remove most of the solid component, and application of the resulting liquids to various filtration surfaces was studied. As woven fabrics, T2731C (manufactured by Shikishima Canvas Co., Ltd.; polyester; double cloth; air permeability, 1.67 cc/cm$^2$·sec) and PP934K (manufactured by Nakao Filter Media Corp.; polypropylene; double cloth; air permeability, 0.3 cc/cm$^2$·sec) were used. As a screen, a 20-μm metal mesh (Iida Kogyo Co., Ltd., twilled) that was cut into a disk shape having a diameter of 4 mm was used. As a non-woven fabric, a non-woven fabric membrane G-2260-3S (manufactured by Toray Industries, Inc.; polyester; air permeability, 11 cc/cm$^2$·sec) was used. The results are shown in Tables 7 and 8. From the results, we found that improvement in the filtration performance is significantly different among the filter materials. Comparison with Example 1 showed that, in a hydrolysate of woody biomass, addition of mannanase is especially effective for filtration using a microfiltration membrane.

TABLE 7

Results of filtration of the hydrothermally treated liquid

| | | Cryptomeria japonica | | | |
|---|---|---|---|---|---|
| Analyzed item | Filter material | Woven fabric T2731C | Woven fabric | Mesh 20 μm | Non-woven fabric G-2260-3S |
| Amount of filtrate (0 to 1 min) | mg | 86.0 | 42.0 | 100.0 | 120.0 |
| Amount of filtrate (1 to 2 min) | mg | 84.0 | 40.0 | 98.0 | 116.0 |

| | | Eucalyptus | | | |
|---|---|---|---|---|---|
| Analyzed item | Filter material | Woven fabric T2731C | Woven fabric | Mesh 20 μm | Non-woven fabric G-2260-3S |
| Amount of filtrate (0 to 1 min) | mg | 90.0 | 46.0 | 102.0 | 116.0 |
| Amount of filtrate (1 to 2 min) | mg | 88.0 | 44.0 | 98.0 | 116.0 |

TABLE 8

Results of filtration of Saccharified Liquid A

| Material | | Cryptomeria japonica | | | |
|---|---|---|---|---|---|
| Analyzed item | Filter material | Woven fabric T2731C | Woven fabric | Mesh 20 μm | Non-woven fabric G-2260-3S |
| Amount of filtrate (0 to 1 min) | mg | 84.0 | 40.0 | 100.0 | 120.0 |
| Amount of filtrate (1 to 2 min) | mg | 84.0 | 40.0 | 100.0 | 118.0 |

| Material | | Eucalyptus | | | |
|---|---|---|---|---|---|
| Analyzed item | Filter material | Woven fabric T2731C | Woven fabric | Mesh 20 μm | Non-woven fabric G-2260-3S |
| Amount of filtrate (0 to 1 min) | mg | 90.0 | 46.0 | 100.0 | 116.0 |
| Amount of filtrate (1 to 2 min) | mg | 86.0 | 42.0 | 98.0 | 114.0 |

Comparative Example 3 Cases of Use of Herbaceous Biomass

For comparison with Example 1, a method of hydrolysis treatment of herbaceous biomass by hydrothermal treatment is described below by way of an example. As a herbaceous biomass, bagasse, which is cane trash, was used. The herbaceous biomass was soaked in water, and processed using an autoclave (manufactured by Nitto Koatsu Co., Ltd.) at 180° C. or 200° C. for 10 minutes. The treatment at 180° C. was carried out as an equivalent treatment since herbaceous hemicellulose is generally known to be more easily degraded than woody biomass. After the treatment, the biomass was allowed to cool to 50° C., and centrifugation (1500 G) was carried out to perform solid-liquid separation into the liquid component (hereinafter referred to as "bagasse hydrothermally treated liquid") and the solid component. The pHs of the bagasse hydrothermally treated liquids were 3.6 and 3.2, respectively. The concentrations observed for each hydrothermally treated liquid were as follows. Components in each hydrothermally treated liquid are shown in Table 9, and the turbidity, the SS concentration, and the total mannose concentration are shown in Table 10.

TABLE 9

Composition of the hydrothermally treated liquid

| Analyzed item | Material Unit | Bagasse Treatment at 180° C. | Treatment at 200° C. |
| --- | --- | --- | --- |
| Xylose | g/L | 13.5 | 11.0 |
| Mannose | g/L | 0.7 | 0.7 |
| Glucose | g/L | 9.0 | 8.0 |
| Mannobiose | g/L | 1.2 | 1.0 |
| Mannotriose | g/L | 0.3 | 0.2 |
| Acetic acid | g/L | 2.0 | 3.0 |
| Formic acid | g/L | 0.7 | 0.8 |
| HMF | g/L | 0.5 | 1.5 |
| Furfural | g/L | 1 | 3.5 |

TABLE 10

Turbidity and SS concentration of the hydrothermally treated liquid

| Analyzed item | Unit | Treatment at 180° C. | Treatment at 200° C. |
| --- | --- | --- | --- |
| Turbidity | NTU | 2200 | 3400 |
| SS concentration | g/L | 5630 | 6400 |
| Total mannose concentration | g/L | 12 | 12 |

The pH of each hydrothermally treated liquid obtained by the solid-liquid separation was adjusted to 5.0 using an aqueous sodium hydroxide solution. To 1 L of the prepared liquid, 0.2 g of mannanase "Mannanase BGM (Amano)" (manufactured by Amano Enzyme Inc.) was added. The enzyme reaction was then carried out at 50° C. for 24 hours. The obtained liquid was once centrifuged at 6000 g to remove most of the solid component, and then subjected to dead-end filtration as an accelerated test using a microfiltration membrane "MEMBRAY TMR140" (registered trademark) (pore size, 0.08 μm), which is a flat membrane whose material is PVDF, manufactured by Toray Industries, Inc., to evaluate the filtration performance of the microfiltration membrane. The membrane was cut into a disk shape having a diameter of 4 mm to provide the filtration area before use. To obtain an index for evaluating the filtration performance, the membrane surface was kept immersed in the liquid while a pressure of 50 kPa was applied thereto. The amount of the liquid that could be filtered during the period from Minute 0 to Minute 1 after the beginning of the pressurization, and the amount of the liquid that could be filtered during the period from Minute 1 to Minute 2 (that is, during the following 1-minute period), were measured. For each of the cases where the hydrolysis treatment was carried out at 180° C. or 200° C., the results on the turbidity before the filtration and the amount of the liquid filtered are shown in Table 11 (hydrothermally treated liquid) and Table 12 (after addition of mannanase).

Based on the result of comparison with Example 1, we found that, while a hydrothermally treated liquid of herbaceous biomass contains mannose, addition of mannanase to the liquid has only a small effect.

TABLE 11

Results of filtration through a microfiltration membrane (before hydrolysis)

| Analyzed item | Unit | 180° C. | 200° C. |
| --- | --- | --- | --- |
| Amount of filtrate (Minute 0 to Minute 1) | mg | 12.0 | 10.0 |
| Amount of filtrate (Minute 1 to Minute 2) | mg | 1.6 | 1.6 |
| Turbidity before filtration | NTU | 255 | 300 |

TABLE 12

Results of filtration through a microfiltration membrane (after addition of mannanase)

| Analyzed item | Unit | 180° C. | 200° C. |
| --- | --- | --- | --- |
| Amount of filtrate (Minute 0 to Minute 1) | mg | 13.0 | 10.0 |
| Amount of filtrate (Minute 1 to Minute 2) | mg | 1.6 | 1.6 |
| Turbidity before filtration | NTU | 240 | 285 |

Example 2 when Steam Explosion Treatment or Dilute Acid Treatment was Carried Out as Hydrolysis Treatment As the woody biomass in Step (1), *Cryptomeria japonica* was used. The biomass was hydrolyzed by steam explosion treatment or dilute acid treatment. The steam explosion treatment was carried out by feeding wood chips of *Cryptomeria japonica* to a steam explosion apparatus (manufactured by Nihon Dennetsu Co., Ltd.; 30-L size), and then introducing steam into the apparatus to keep the pressure at 3.5 MPa for 2.5 minutes. The steam-explosion-treated product of *Cryptomeria japonica* was immediately placed in water, and additional water was further added thereto to a solid content of 10% by mass. The product was then stirred, and centrifuged at 1500 G for 1 minute to separate the solid component and the liquid component from each other. This liquid component is referred to as "explosion-treated hydrolysate".

The dilute acid treatment was carried out by soaking wood chips of *Cryptomeria japonica* in 0.5% aqueous sulfuric acid solution at a solid concentration of 20 wt %, and then autoclaving the wood chips at a temperature of 170° C. for 10 minutes (using an autoclave manufactured by Nitto Koatsu Co., Ltd.). Thereafter, centrifugation was carried out at 1500 G for 1 minute to separate the solid component and the liquid component from each other. The obtained liquid component is referred to as "dilute-acid-treated hydrolysate". The composition, the SS concentration, and the turbidity of each liquid component are shown in Tables 13 and 14.

TABLE 13

Compositions of the steam explosion-treated hydrolysate and the dilute acid-treated hydrolysate

| Analyzed item | Unit | Steam explosion treatment | Dilute acid treatment |
| --- | --- | --- | --- |
| Xylose | g/L | 2.5 | 5.8 |
| Mannose | g/L | 0.6 | 2.0 |
| Glucose | g/L | 0.3 | 0.6 |
| Mannobiose | g/L | 0.7 | 2.0 |
| Mannotriose | g/L | 0.3 | 1.2 |
| Acetic acid | g/L | 1.5 | 1.5 |
| Formic acid | g/L | 0.6 | 0.5 |
| HMF | g/L | 0.3 | 0.2 |
| Furfural | g/L | 0.5 | 0.4 |

TABLE 14

Turbidity and SS concentration of the steam explosion-treated hydrolysate and the dilute acid-treated hydrolysate

| Analyzed item | Unit | Steam explosion treatment | Dilute acid treatment |
| --- | --- | --- | --- |
| Turbidity | NTU | 654 | 563 |
| SS concentration | g/L | 1230 | 966 |
| Total mannose concentration | g/L | 13 | 20 |

The pHs of the dilute-acid-treated hydrolysate and the explosion-treated hydrolysate obtained were adjusted to 5.0 using an aqueous sodium hydroxide solution. Each hydrolysate was then divided into two portions, and 0.2 g of mannanase "Mannanase BGM (Amano)" (manufactured by Amano Enzyme Inc.) was added to one of these portions (liquid volume, 1 L), and 0.2 g of "Mannanase BGM (Amano)" (manufactured by Amano Enzyme Inc.) as well as 2 mL of cellulase "ACCELLERASE DUET" (manufactured by Danisco Japan) were added to the other portion (liquid volume, 1 L). The enzyme reaction was then carried out at 50° C. for 24 hours. Thereafter, by the same methods as in Example 1, evaluation of the filtration performance of the microfiltration membrane and measurement of the turbidity before the filtration were carried out. The results are shown in Tables 15 and 16. The amount of mannanase added, as calculated with respect to the total amount of mannose (g) contained in each hydrolysate, was 167 Units/g in the liquid prepared from the explosion-treated hydrolysate, and 167 Units/g in the liquid prepared from the dilute-acid-treated hydrolysate.

TABLE 15

Results of filtration through a microfiltration membrane (only mannanase)

| Analyzed item | Unit | Steam explosion treatment | Dilute acid treatment |
| --- | --- | --- | --- |
| Amount of filtrate (0 to 1 min) | mg | 24.0 | 20.0 |
| Amount of filtrate (1 to 2 min) | mg | 19.6 | 17.6 |
| Turbidity before filtration | NTU | 106 | 92 |

TABLE 16

Results of filtration through a microfiltration membrane (addition of mannanase and cellulase)

| Analyzed item | Unit | Steam explosion treatment | Dilute acid treatment |
| --- | --- | --- | --- |
| Amount of filtrate (0 to 1 min) | mg | 32.0 | 24.0 |
| Amount of filtrate (1 to 2 min) | mg | 24.0 | 19.2 |
| Turbidity before filtration | NTU | 92 | 90 |

Comparative Example 4 When Steam Explosion Treatment or Dilute Acid Treatment was Carried Out as Hydrolysis Treatment Each hydrolysate whose pH was adjusted to 5 obtained in Example 2 was subjected to evaluation of the filtration performance and measurement of the turbidity before the filtration, by the same methods as in Example 1. The results are shown in Table 17.

TABLE 17

Results of filtration through a microfiltration membrane (hydrolysate, no addition of enzyme)

| Analyzed item | Unit | Steam explosion treatment | Dilute acid treatment |
| --- | --- | --- | --- |
| Amount of filtrate (0 to 1 min) | mg | 4.8 | 12.8 |
| Amount of filtrate (1 to 2 min) | mg | 2.4 | 9.6 |
| Turbidity before filtration | NTU | 145 | 104 |

As a result of comparison with Examples 1 and 2, we found that the desired effect can be obtained also for hydrolysates obtained by steam explosion treatment or dilute acid treatment of woody biomass.

Example 3 Study on Amount of Mannanase Added

Each of liquids prepared by adding 0.28 mg, 2.8 mg, 28 mg, 280 mg, or 2.8 g of "Mannanase BGM (Amano)" (manufactured by Amano Enzyme Inc.) (galactomannan activity concentration, 10,000 Units/g) to 1 L of the hydrothermally treated liquid obtained by the hydrothermal treatment of wood chips of *Cryptomeria japonica* used in Example 1 (pH 5, total mannose concentration, 28 g/L) was subjected to evaluation of the filtration performance of the microfiltration membrane and measurement of the turbidity before the filtration by the same methods as in Example 1. The results are shown in Table 18. As described in Table 18, the amount of mannanase added was 0.01 Unit/g, 0.1 Unit/g, 1.0 Unit/g, 10 Units/g, 100 Units/g, or 1000 Units/g with respect to the total amount of mannose (g) contained in the hydrolysate.

TABLE 18

| | | \multicolumn{6}{c}{Study on the amount of mannanase added} |
|---|---|---|---|---|---|---|---|
| Amount of mannanase added | mg/L | 0.028 | 0.28 | 2.8 | 28 | 280 | 2800 |
| | Unit/L | 0.28 | 2.8 | 28 | 280 | 2800 | 28000 |
| | U/g (Total mannose) | 0.01 | 0.1 | 1.0 | 10 | 100 | 1000 |
| Amount of filtrate (0 to 1 min) | mg | 1.5 | 5.2 | 16.0 | 17.6 | 17.6 | 17.6 |
| Amount of filtrate (1 to 2 min) | mg | 1.2 | 4.6 | 14.4 | 14.4 | 14.4 | 14.4 |
| Turbidity before filtration | NTU | 212 | 189 | 168 | 152 | 150 | 150 |

Reference Example 7 Analysis of Amount of Mannanase in Cellulase Enzyme Liquid

To investigate whether the results were influenced by the effect of mannanase contained in the cellulase, the galactomannan activity of the cellulase enzyme liquid "ACCELLERASE DUET" (manufactured by Danisco Japan) was measured. As a result, the activity was 0.084 Unit/mL. Since this corresponds to 0.006 Unit/g, the influence of mannanase in the cellulase is very small.

Example 4 Test for Long-Term Stability of Microfiltration Membrane Treatment—Inorganic Membrane, Organic Membrane The Saccharified Liquids A and B derived from wood chips of *Cryptomeria japonica* obtained in Example 1 were subjected to cross-flow filtration through microfiltration membranes to evaluate their long-term stabilities. This study was carried out with each of an inorganic membrane and an organic membrane. As the organic membrane, a microfiltration membrane "TORAYFIL HFM" (manufactured by Toray Industries, Inc.; material, PVDF; pore size, 0.1 μm) was used. As the inorganic membrane, a microfiltration membrane "MEMBRALOX" (manufactured by PALL; material, pore size, 0.2 μm) was used. Filtration was carried out for a membrane area of 0.24 m². Forty liters each of Saccharified Liquids A and B were provided, and each of these was filtered with a membrane surface linear velocity of 30 cm/sec. and a membrane filtration rate of 0.5 m/D until the filtration pressure (transmembrane pressure difference) reached 100 kPa. Thereafter, the membrane was washed with water, and the remaining Saccharified Liquids A and B were subjected to the filtration again until the filtration pressure reached 100 kPa. The filtration pressure value measured immediately after the beginning of the operation, and the filtration pressure value measured immediately after the restart of the operation following the washing with water, are shown in Table 19. The length of time required for reaching 100 kPa is shown in Table 20.

TABLE 19

| | | \multicolumn{4}{c}{Filtration pressure value} |
|---|---|---|---|---|---|
| | | \multicolumn{2}{c}{Saccharified Liquid A} | \multicolumn{2}{c}{Saccharified Liquid B} |
| | Unit | Organic membrane | Inorganic membrane | Organic membrane | Inorganic membrane |
| Immediately after beginning | kPa | 3 | 9 | 2 | 8 |
| Immediately after restart following washing with water | kPa | 6 | 9 | 4 | 8 |

TABLE 20

| | | \multicolumn{4}{c}{Time required for reaching 100 kPa} |
|---|---|---|---|---|---|
| | | \multicolumn{2}{c}{Saccharified Liquid A} | \multicolumn{2}{c}{Saccharified Liquid B} |
| | Unit | Organic membrane | Inorganic membrane | Organic membrane | Inorganic membrane |
| Immediately after beginning | Minute | 290 | 95 | 384 | 107 |
| Immediately after restart following washing with water | Minute | 210 | 87 | 325 | 98 |

Comparative Example 4 Test for Long-Term Stability of Microfiltration Membrane Treatment—Filtration without Addition of Enzyme The hydrothermally treated liquid derived from wood chips of *Cryptomeria japonica* (pH 5) obtained in Example 1 was subjected to cross-flow filtration through microfiltration membranes, and their long-term stabilities were evaluated in the same manner as in Example 4. The filtration pressure value measured immediately after the beginning of the operation, and the filtration pressure value measured immediately after the restart of the operation following the washing with water, are shown in Table 21. The length of time required for reaching 100 kPa is shown in Table 22.

TABLE 21

Filtration pressure value

| | | Hydrothermally treated liquid | | Saccharified Liquid C | |
|---|---|---|---|---|---|
| | Unit | Organic membrane | Inorganic membrane | Organic membrane | Inorganic membrane |
| Immediately after beginning | kPa | 5 | 11 | 4 | 11 |
| Immediately after restart following washing with water | kPa | 10 | 12 | 9 | 12 |

TABLE 22

Time required for reaching 100 kPa

| | | Hydrothermally treated liquid | | Saccharified Liquid C | |
|---|---|---|---|---|---|
| | Unit | Organic membrane | Inorganic membrane | Organic membrane | Inorganic membrane |
| Immediately after beginning | Minute | 32 | 63 | 34 | 65 |
| Immediately after restart following washing with water | Minute | 25 | 59 | 27 | 57 |

By comparison with Example 4, we found that the pressure immediately after the beginning is high, and that the filtration pressure reaches 100 kPa in a short time, so that there is a high risk of fouling. We also found that the effect is more remarkable when an organic membrane is used as the microfiltration membrane.

Example 5 Separation of Mannobiose and Mannotriose from Enzyme-Treated Liquid

Saccharified Liquid B was subjected to microfiltration membrane treatment under the conditions in Example 1, and further to filtration through a SEPA II cross-flow filtration device, manufactured by GE, to which an ultrafiltration membrane PW (manufactured by GE; material, polyethersulfone; molecular weight cutoff, 10,000) was attached. As a result, a sugar liquid having the composition shown in Table 23 was obtained.

TABLE 23

Composition of the hydrothermally treated liquid/ultrafiltration membrane (MW: 10,000)-treated liquid

| Analyzed item | Unit | Filtrate |
|---|---|---|
| Xylose | g/L | 10.7 |
| Mannose | g/L | 9.6 |
| Glucose | g/L | 6.1 |
| Mannobiose | g/L | 10.2 |
| Mannotriose | g/L | 2.4 |
| Acetic acid | g/L | 2.0 |
| Formic acid | g/L | 0.7 |
| HMF | g/L | 0.6 |
| Furfural | g/L | 1.2 |

The resulting filtrate was divided into two portions, and each portion was filtered through a SEPA II cross-flow filtration device, manufactured by GE, to which an ultrafiltration membrane NTR-7450 (manufactured by Nitto Denko Corporation; material, sulfonated polyethersulfone; molecular weight cutoff, 600 to 800) or SPE1 (manufactured by Synder; material, polyethersulfone; molecular weight cutoff, 1000) was attached. By this, each portion was 6-fold concentrated. The results obtained for each membrane are shown in Tables 24 and 25.

TABLE 24

Composition of the liquid separated with "NTR-7450"

| Analyzed item | Unit | Concentrate side | Permeate |
|---|---|---|---|
| Xylose | g/L | 12.2 | 10.4 |
| Mannose | g/L | 10.6 | 9.4 |
| Glucose | g/L | 7.1 | 5.9 |
| Mannobiose | g/L | 51.2 | 2.0 |
| Mannotriose | g/L | 13.4 | 0.2 |
| Acetic acid | g/L | 2.0 | 2.0 |
| Formic acid | g/L | 0.7 | 0.7 |
| HMF | g/L | 0.6 | 0.6 |
| Furfural | g/L | 1.2 | 1.2 |

TABLE 25

Composition of the liquid separated with "SPE1"

| Analyzed item | Unit | Concentrate side | Permeate |
|---|---|---|---|
| Xylose | g/L | 10.7 | 10.7 |
| Mannose | g/L | 9.6 | 9.6 |
| Glucose | g/L | 6.1 | 6.1 |
| Mannobiose | g/L | 46.2 | 3.0 |
| Mannotriose | g/L | 11.9 | 0.5 |
| Acetic acid | g/L | 2.0 | 2.0 |
| Formic acid | g/L | 0.7 | 0.7 |
| HMF | g/L | 0.6 | 0.6 |
| Furfural | g/L | 1.2 | 1.2 |

Although the concentrations of the components in the concentrate side were not less than those shown in Table 23, liquids containing large amounts of mannobiose and mannotriose could be obtained by water-adding filtration, that is, diafiltration.

Example 6 Continuous Filtration with Ultrafiltration Membrane

The following is an example in which saccharification and recovery of enzyme are continuously carried out using the hydrothermally treated liquid prepared in Example 1 (pH 5). In a 1-L tank, 500 mL of the hydrothermally treated liquid was retained, and 0.1 g of "Mannanase BGM (Amano)" (manufactured by Amano Enzyme Inc.) and 1 mL of cellulase "ACCELLERASE DUET" (manufactured by Danisco Japan) were added into the tank, followed by continuously carrying out filtration for 10 hours. An ultrafiltration membrane "MICROZA SLP-0053" (manufactured by Asahi Kasei Corporation; material, polysulfone; molecular weight cutoff, 10,000) was used. While the tank was kept at 50° C., only circulation between the module and the tank was carried out during the first four hours after the beginning of the operation. Thereafter, filtration was carried out at 5 mL/minute while the hydrothermally treated liquid was supplied into the tank at the same rate, 5 mL/minute. The temperature in the tank was constantly kept at 50° C. At Hour 0, Hour 1, Hour 5, and Hour 10 after the beginning of the filtration, the composition of the filtrate as a sugar liquid was as shown in Table 26. Thus, we found that sugar liquids having almost the same composition can be always obtained. That is, in a state where the enzyme was retained in the feed side of the membrane and the tank by recovery of mannanase and cellulase by ultrafiltration, the hydrothermally treated liquid could be continuously filtered while mannobiose and manno-oligosaccharides were produced. The results on the concentrations of mannobiose and manno-oligosaccharides were equivalent to those shown in Table 23 of Example 5. Thus, we found that the saccharification and the enzyme recovery, as well as the membrane treatment can be integrated together. Since no increase in the operating pressure was found during the membrane treatment, we found that the process can be continuously operated.

TABLE 26

Composition of the membrane filtrate obtained by continuous membrane treatment

| Analyzed item | Unit | Hour 0 | Hour 1 | Hour 5 | Hour 10 |
|---|---|---|---|---|---|
| Xylose | g/L | 10.0 | 10.0 | 10.0 | 10.0 |
| Arabinose | g/L | 4.8 | 4.8 | 4.8 | 4.8 |
| Mannose | g/L | 9.2 | 9.2 | 9.2 | 9.2 |
| Glucose | g/L | 5.2 | 5.2 | 5.2 | 5.2 |
| Galactose | g/L | 3.6 | 3.6 | 3.6 | 3.6 |
| Mannobiose | g/L | 9.6 | 9.6 | 9.6 | 9.6 |
| Mannotriose | g/L | 1.8 | 1.8 | 1.8 | 1.8 |
| Acetic acid | g/L | 2.0 | 2.0 | 2.0 | 2.0 |
| Formic acid | g/L | 0.7 | 0.7 | 0.7 | 0.7 |
| HMF | g/L | 0.6 | 0.6 | 0.6 | 0.6 |
| Furfural | g/L | 1.2 | 1.2 | 1.2 | 1.2 |

Comparative Example 6 Continuous Filtration with Ultrafiltration Membrane (Liquid Component)

By the same method as in Example 6, filtration was carried out without addition of enzyme. As a result, after 90 minutes of the filtration, production of the filtrate stopped, and the filtration became impossible.

Example 7 When Agricultural and Forestry Waste Oil Palm Empty Fruit Bunch was Used A method of carrying out the hydrolysis in Step (1) by the same method as in Examples 1 or 2 (that is, hydrothermal treatment, steam explosion treatment, or dilute acid treatment) except that oil palm empty fruit bunch is used as the woody biomass is described below by way of an example similarly to the methods in Examples 1 and 2.

The hydrothermal treatment was carried out by soaking oil palm empty fruit bunch in water, and carrying out treatment using an autoclave (manufactured by Nitto Koatsu Co., Ltd.) at 200° C. for 10 minutes with stirring. After the treatment, the biomass was allowed to cool to 50° C., and centrifugation (1500 G) was carried out to perform solid-liquid separation into the liquid component (hereinafter referred to as "hydrothermally treated liquid") and the solid component. The pH of the hydrothermally treated liquid was 3.8.

The steam explosion treatment was carried out by feeding oil palm empty fruit bunch, and then introducing steam thereto, followed by keeping the pressure at 3.5 MPa for 2.5 minutes. The steam-explosion-treated product of *Cryptomeria japonica* was immediately placed in water, and additional water was further added thereto to a solid content of 10% by mass. The product was then stirred, and centrifuged at 1500 G for 1 minute to separate the solid component and the liquid component from each other. This liquid component is referred to as "explosion-treated hydrolysate".

The dilute acid treatment was carried out by soaking oil palm empty fruit bunch in 0.5% aqueous sulfuric acid solution at a solid concentration of 20 wt %, and then autoclaving the soaked oil palm empty fruit bunch at a temperature of 170° C. for 10 minutes (using an autoclave manufactured by Nitto Koatsu Co., Ltd.). Thereafter, centrifugation was carried out at 1500 G for 1 minute to separate the solid component and the liquid component from each other. The obtained liquid component is referred to as "dilute-acid-treated hydrolysate". The composition, the SS concentration, and the turbidity of each liquid component are shown in Tables 27 and 28.

TABLE 27

Composition of the liquid component

| Analyzed item | Unit | Hydrothermal treatment | Steam explosion treatment | Dilute acid treatment |
|---|---|---|---|---|
| Xylose | g/L | 12.0 | 2.5 | 5.8 |
| Mannose | g/L | 0.8 | 0.4 | 2.0 |
| Glucose | g/L | 2.0 | 0.3 | 0.6 |
| Mannobiose | g/L | 0.2 | 0.7 | 2.0 |
| Mannotriose | g/L | 0.1 | 0.3 | 1.2 |
| Acetic acid | g/L | 1.8 | 1.5 | 1.5 |
| Formic acid | g/L | 0.4 | 0.6 | 0.5 |
| HMF | g/L | 0.4 | 0.3 | 0.2 |
| Furfural | g/L | 4.0 | 0.5 | 0.4 |

TABLE 28

Turbidity and SS concentration of the hydrothermally treated liquid

| Analyzed item | Unit | Hydrothermal treatment | Steam explosion treatment | Dilute acid treatment |
|---|---|---|---|---|
| Turbidity | NTU | 2390 | 1848 | 2420 |
| SS concentration | g/L | 6800 | 5056 | 7246 |
| Total mannose concentration | g/L | 25 | 30 | 40 |

The pHs of the hydrothermally treated liquid, the explosion-treated hydrolysate, and the dilute-acid-treated hydrolysate obtained were adjusted to 5.0 using an aqueous sodium hydroxide solution. Each hydrolysate was then divided into two portions, and 0.2 g of mannanase "Mannanase BGM (Amano)" (manufactured by Amano Enzyme Inc.) was added to one of these portions (liquid volume, 1 L), and 0.2 g of "Mannanase BGM (Amano)" (manufactured by Amano Enzyme Inc.) as well as 2 mL of cellulase "ACCELLERASE DUET" (manufactured by Danisco Japan) were added to the other portion (liquid volume, 1 L). The enzyme reaction was then carried out at 50° C. for 24 hours. The resulting liquids are referred to as Saccharified Liquid E and Saccharified Liquid F, respectively. Originally, measurement by cross-flow filtration should be carried out, but, for simplicity of the study, the solid component was once mostly removed by centrifugation at 6000 G, and then dead-end filtration was carried out as an accelerated test using a microfiltration membrane "MEMBRAY TMR140" (registered trademark) (pore size, 0.08 μm), which is a flat membrane whose material is PVDF, manufactured by Toray Industries, Inc., to evaluate the filtration performance of the microfiltration membrane. The membrane was cut into a disk shape having a diameter of 4 mm to provide the filtration area before use. To obtain an index for evaluating the filtration performance, the membrane surface was kept immersed in the liquid while a pressure of 50 kPa was applied thereto. The amount of the liquid that could be filtered during the period from Minute 0 to Minute 1 after the beginning of the pressurization, and the amount of the liquid that could be filtered during the period from Minute 1 to Minute 2 (that is, during the following 1-minute period), were measured. The results on the turbidity before the filtration and the amount of the liquid filtered for each sample are shown in Table 29 (for Saccharified Liquid E) and Table 30 (for Saccharified Liquid F). The amount of the mannanase added for the preparation of Saccharified Liquid E or F was 80 Units/g in the hydrothermal treatment, 67 Units/g in the steam explosion treatment, and 50 Unit/g in the dilute acid treatment with respect to the total amount of mannose (g) contained in each liquid component.

TABLE 29

Results of filtration through a microfiltration membrane (Saccharified Liquid E)

| Analyzed item | Unit | Hydrothermal treatment | Steam explosion treatment | Dilute acid treatment |
|---|---|---|---|---|
| Amount of filtrate (0 to 1 min) | mg | 8.6 | 9.0 | 12.1 |
| Amount of filtrate (1 to 2 min) | mg | 5.4 | 6.4 | 6.4 |
| Turbidity before filtration | NTU | 242 | 252 | 100 |

TABLE 30

Results of filtration through a microfiltration membrane (Saccharified Liquid F)

| Analyzed item | Unit | Hydrothermal treatment | Steam explosion treatment | Dilute acid treatment |
|---|---|---|---|---|
| Amount of filtrate (0 to 1 min) | mg | 20.0 | 20.0 | 21.0 |
| Amount of filtrate (1 to 2 min) | mg | 12.2 | 14.2 | 18.2 |
| Turbidity before filtration | NTU | 122 | 166 | 122 |

Comparative Example 7 Components in Hydrolysate of Oil Palm Empty Fruit Bunch: Cases without Addition of Enzyme The hydrothermally treated liquid, the explosion-treated hydrolysate, and the dilute-acid-treated hydrolysate of oil palm empty fruit bunch obtained in Example 7 were subjected to cross-flow filtration using a microfiltration membrane in the same manner as in Example 7. For each hydrolysate, evaluation of the filtration performance and measurement of the turbidity before the filtration were carried out by the same methods as in Example 1. The results are shown in Table 31.

TABLE 31

Results of filtration through a microfiltration membrane (no addition)

| Analyzed item | Unit | Hydrothermal treatment | steam explosion treatment | Dilute acid treatment |
|---|---|---|---|---|
| Amount of filtrate (0 to 1 min) | mg | 7.2 | 7.4 | 10.8 |
| Amount of filtrate (1 to 2 min) | mg | 4.2 | 4.4 | 5.6 |
| Turbidity before filtration | NTU | 300 | 270 | 120 |

As a result of comparison with Example 7, we found that the desired effect can be obtained also for the liquid component obtained by hydrolysis treatment of oil palm empty fruit bunch.

Comparative Example 8 When Mannanase was Applied to Agricultural and Forestry Waste Oil Palm Empty Fruit Bunch without Carrying Out Hydrolysis Treatment When the oil palm empty fruit bunch studied in Example 7 was subjected to mannanase treatment without carrying out hydrolysis treatment is described below. The total amount of mannose present in the oil palm empty fruit bunch (based on the dry weight) was found to be 25 mg/g-dry oil palm empty fruit bunch as a result of analysis using the method in Reference Example 6.

Water was added to the oil palm empty fruit bunch used in Example 7 to a solid concentration of 20%, and the pH of the resulting mixture was adjusted to 5.0 with 3 N sodium acetate with stirring. The mixture was then divided into three portions. Subsequently, 0.2 g of mannanase "Mannanase BGM (Amano)" (manufactured by Amano Enzyme Inc.) was added to one of these portions to prepare Saccharified Liquid G (liquid volume, 1 L); 0.2 g of "Mannanase BGM (Amano)" (manufactured by Amano Enzyme Inc.) as well as 2 mL of cellulase "ACCELLERASE DUET" (manufactured by Danisco Japan) were added to another portion to prepare Saccharified Liquid H (liquid volume, 1 L); and the remaining portion was provided as a liquid to which no enzyme was added (liquid volume, 1 L). The pHs of Saccharified Liquid G, Saccharified Liquid H, and the liquid to which no enzyme was added were adjusted to 5.0, and each liquid was kept at 50° C. for 24 hours. After the reaction, centrifugation was carried out at 6000 G to remove most of the solid component, and each liquid was subjected to evaluation of the filtration performance of the microfiltration membrane by the accelerated test by the same method as in Example 6. Similarly to Example 6, the amount of the liquid that could be filtered during the period from Minute 0 to Minute 1 after the beginning of the pressurization, and the amount of the liquid that could be filtered during the period from Minute 1 to Minute 2 (that is, during the following 1-minute period), were measured. The results on the turbidity before the filtration and the amount of the liquid filtered for each sample are shown in Table 32. The concentrations of mannose, mannobiose, and mannotriose are also shown in the table.

TABLE 32

Results of filtration through a microfiltration membrane (Saccharified Liquids G and H)

| Analyzed item | Unit | No addition | Saccharified Liquid G | Saccharified Liquid H |
|---|---|---|---|---|
| Amount of filtrate (0 to 1 min) | mg | 42.0 | 20.0 | 20.0 |
| Amount of filtrate (1 to 2 min) | mg | 35.0 | 15.0 | 15.0 |
| Turbidity before filtration | NTU | 85 | 85 | 85 |
| Mannose concentration | g/L | Undetected | 0.1 | 0.1 |
| Mannobiose concentration | g/L | Undetected | Undetected | Undetected |
| Mannotriose concentration | g/L | Undetected | Undetected | Undetected |

From the results shown in the table, we found that hydrolysis treatment of the oil palm empty fruit bunch itself is not effective, and that the addition of the enzymes leads to a decreased filtration performance.

INDUSTRIAL APPLICABILITY

High-quality sugars (monosaccharides, mannobiose, and mannotriose) can be obtained from woody biomass at low cost, and the monosaccharide liquid can be used as a fermentation feedstock.

The invention claimed is:

1. A method of producing a sugar liquid, comprising:
   (A) degrading fouling substances derived from woody biomass included in a liquid component obtained by hydrolysis treatment of the woody biomass by adding mannanase and then reacting the mannanase with the liquid component and obtaining a saccharified liquid; and
   (B) filtering the saccharified liquid in Step (A) through a microfiltration membrane to collect a sugar liquid from a permeate side,
   wherein the microfiltration membrane in Step (B) is a microfiltration membrane having an average pore size of 0.01 to 0.2 µm; and wherein the amount of mannanase added is effective in degrading the fouling substances.

2. The method according to claim 1, wherein the woody biomass is coniferous biomass.

3. The method according to claim 1, wherein the hydrolysis treatment in Step (A) is one or more selected from the group consisting of hydrothermal treatment, steam explosion treatment, and dilute acid treatment.

4. The method according to claim 1, further comprising in the Step (A), reacting cellulase with the liquid component.

5. The method according to claim 1, wherein a functional B surface(s) of a material(s) of the microfiltration membrane in Step (B) is/are an organic membrane(s).

6. The method according to claim 1, further comprising:
   (C) filtering the sugar liquid obtained in Step (B) through an ultrafiltration membrane having a molecular weight cutoff of 300 to 1000, to collect a sugar liquid containing mannobiose and/or mannotriose from a feed side, and to collect a sugar liquid containing a monosaccharide from the permeate side.

7. The method according to claim 1, further comprising carrying out an ultrafiltration membrane treatment in Step (B); and using an enzyme component(s) collected from a feed side of the ultrafiltration membrane in Step (A).

8. A method of producing a sugar liquid, comprising:
   (A) degrading fouling substances derived from woody biomass included in a liquid component obtained by hydrolysis treatment of the woody biomass by adding mannanase and then reacting mannanase with the liquid component and obtaining a saccharified liquid; and
   (B) filtering the saccharified liquid in Step (A) through a microfiltration membrane to collect a sugar liquid from a permeate side,
   wherein, in Step (A), the amount of mannanase added is not less than 0.01 Unit/g with respect to the total amount of mannose (g) contained in the liquid component; and wherein the amount of mannanase added is effective in degrading the fouling substances.

9. A method of producing a sugar liquid, comprising:
   (A) degrading fouling substances derived from woody biomass included in a liquid component obtained by hydrolysis treatment of the woody biomass by adding mannanase and then reacting mannanase with the liquid component and obtaining a saccharified liquid; and
   (B) filtering the saccharified liquid in Step (A) through a microfiltration membrane to collect a sugar liquid from a permeate side; and wherein the amount of mannanase added is effective in degrading the fouling substances.

\* \* \* \* \*